United States Patent
McEwen et al.

(10) Patent No.: US 7,331,977 B2
(45) Date of Patent: *Feb. 19, 2008

(54) ADAPTIVE TOURNIQUET CUFF SYSTEM

(76) Inventors: James A. McEwen, 10551 Bamberton Drive, Richmond, B.C. (CA) V7A 1K6; Kevin B. Inkpen, 1950 Graveley Street, Vancouver, B.C. (CA) V5L 3B4; Michael Jameson, 2365 Badger Rd., North Vancouver, B.C. (CA) V7G 1S9

( * ) Notice: Subject to any disclaimer, the term of this patent is extended or adjusted under 35 U.S.C. 154(b) by 338 days.

This patent is subject to a terminal disclaimer.

(21) Appl. No.: 10/358,412

(22) Filed: Feb. 4, 2003

(65) Prior Publication Data

US 2003/0167070 A1    Sep. 4, 2003

Related U.S. Application Data

(63) Continuation-in-part of application No. 09/930,341, filed on Aug. 14, 2001, now Pat. No. 6,682,547.

(51) Int. Cl.
A61B 17/00 (2006.01)
(52) U.S. Cl. ..................................... 606/202
(58) Field of Classification Search ............... 606/202, 606/10, 11, 12; 600/498, 499, 132; 356/425
See application file for complete search history.

(56) References Cited

U.S. PATENT DOCUMENTS

| | | | |
|---|---|---|---|
| 2,199,408 A | 5/1940 | La Liberte |
| 4,469,099 A | 9/1984 | McEwen |
| 4,479,494 A | 10/1984 | McEwen |
| 4,501,280 A | 2/1985 | Hood |
| 4,605,010 A | 8/1986 | McEwen |
| 4,635,635 A | 1/1987 | Robinette-Lehman |
| 4,917,500 A | 4/1990 | Lugos |
| 4,979,953 A | 12/1990 | Spence |
| 5,022,403 A | 6/1991 | LaViloa |

(Continued)

FOREIGN PATENT DOCUMENTS

EP    0 473 987    3/1992

(Continued)

OTHER PUBLICATIONS

International Search Report and Written Opinion for PCT/CA2004/000106; EPO; May 25, 2004; 11 pages.

*Primary Examiner*—Eduardo C. Robert
*Assistant Examiner*—David Comstock
(74) *Attorney, Agent, or Firm*—Hancock Hughey LLP (57) ABSTRACT

An adaptive tourniquet cuff system comprises: a tourniquet cuff having a physical characteristic and including an inflatable bladder of a length greater than the circumference of a limb at a selected location; a cuff connector carried on the cuff and communicating pneumatically with the bladder for releasably connecting to a tourniquet instrument to establish a gas-tight passageway between the bladder and the tourniquet instrument; and an identifying collar including identification means indicative of the physical characteristic and detectable by the tourniquet instrument upon establishment of the gas-tight passageway. The tourniquet instrument may supply gas to the bladder through the gas-tight passageway at a pressure sufficient to stop arterial blood flow into the limb distal to the cuff at the selected location, and may adapt its operation in response to the detected physical characteristic of the cuff.

12 Claims, 5 Drawing Sheets

U.S. PATENT DOCUMENTS

| | | |
|---|---|---|
| 5,048,536 A | 9/1991 | McEwen |
| 5,060,654 A | 10/1991 | Malkamaki |
| 5,150,174 A | 9/1992 | Ryczek |
| 5,181,522 A | 1/1993 | McEwen |
| 5,193,549 A | 3/1993 | Bellin |
| 5,312,431 A | 5/1994 | McEwen |
| 5,411,518 A | 5/1995 | Goldstein |
| 5,413,582 A | 5/1995 | Eaton |
| 5,454,831 A | 10/1995 | McEwen |
| 5,578,055 A | 11/1996 | McEwen |
| 5,584,853 A | 12/1996 | McEwen |
| 5,649,954 A | 7/1997 | McEwen |
| 5,681,307 A | 10/1997 | McMahon |
| 5,690,672 A | 11/1997 | Cohen |
| 5,733,304 A | 3/1998 | Spence |
| 5,741,295 A | 4/1998 | McEwen |
| 5,855,589 A | 1/1999 | McEwen |
| 5,911,735 A | 6/1999 | McEwen |
| 5,931,853 A | 8/1999 | McEwen |
| 5,935,146 A | 8/1999 | McEwen |
| 6,124,936 A | 9/2000 | Okamato |
| 6,213,939 B1 | 4/2001 | McEwen |
| 6,450,966 B1 | 9/2002 | Hanna |
| 6,506,206 B1 | 1/2003 | Guzman |

FOREIGN PATENT DOCUMENTS

| | | |
|---|---|---|
| EP | 1016379 A1 | 12/1999 |
| WO | WO 95/26703 | 10/1995 |
| WO | WO 00/06904 | 2/2000 |
| WO | WO 03/015641 | 2/2003 |

ADAPTIVE TOURNIQUET CUFF SYSTEM

CROSS REFERENCE TO RELATED APPLICATION

This application is a continuation-in-part of U.S. patent application No. 09/920,341, filed Aug. 14, 2001, now U.S. Pat. No. 6,682,547.

BACKGROUND

The use of an inflatable tourniquet cuff to occlude blood flow into a subject's limb, thereby providing a bloodless surgical field in the portion of the limb distal to the cuff over a period of time suitably long for the performance of a surgical procedure, is well known in surgical practice. Tourniquet systems typically include an inflatable cuff for encircling a limb at a selected location and a tourniquet instrument for maintaining the pressure in the cuff near a selected pressure. Such tourniquet instruments of the prior art typically contain, or connect to, a source of pressurized gas and include a pressure regulating mechanism for controlling and maintaining the pressure of the gas supplied to the tourniquet cuff near the selected pressure.

Typically a variety of cuff sizes are provided so that a cuff that overlaps itself when encircling the limb may be selected, thereby ensuring that pressure is applied to the limb around its entire circumference. Cuffs are also provided in a variety of shapes, widths, materials, configurations and other physical characteristics as required for different types of patients, limb locations, and surgical procedures.

Other physical characteristics of the cuff may be the manufacturer of the cuff, the state of sterility or non-sterility of the cuff as supplied by the manufacturer, the size, shape and potential volume of the inflatable bladder or chamber within the cuff, the number of uses the cuff is designed for, and any physical changes that may have resulted from surgical use and any reprocessing after use.

Other physical characteristics of the cuff may be the manufacturer of the cuff, the state of sterility or non-sterility of the cuff as supplied by the manufacturer, the size, shape and potential volume of the inflatable bladder or chamber within the cuff, the number of uses the cuff is designed for, and any physical changes that may have resulted from surgical use and any reprocessing after use.

Modern tourniquet instruments of the prior art employ digital electronic technology in the regulation of pressure for the tourniquet cuff and in the detection of certain hazardous conditions. However the pressure selected at the tourniquet instrument for regulation within the tourniquet cuff has often been very arbitrarily chosen by surgical staff, regardless of the type or size of cuff connected to the tourniquet instrument. More recently, some surgical staff are selecting lower tourniquet pressures based on the surgeon's estimate of the minimum pressure required to safely occlude blood flow past the cuff in a specific patient. This minimum safe pressure is affected by a number of variables, including the physical characteristics of the specific tourniquet cuff attached to the patient, and so providing a convenient, reliable and automatic means for the tourniquet instrument to identify certain physical characteristics of that cuff (such as length, width, and type) is useful for adapting the estimate of the minimum safe pressure, either manually with the involvement of the surgical staff or automatically by the tourniquet instrument connected to the cuff. For example, if a wide cuff is identified as being connected to the tourniquet instrument, then the instrument may display instructions to the surgeon to select a lower tourniquet pressure setting than the arbitrary pressure setting that might otherwise be used, to reduce the likelihood of pressure related injury while still stopping blood flow effectively, or the tourniquet instrument may automatically adapt the tourniquet pressure setting to that lower pressure.

Automatic identification of the specific cuff connected to the tourniquet instrument also allows adaptation of the settings of important operating and safety parameters of the tourniquet instrument and system as a whole. For example, if a very small pediatric tourniquet cuff is automatically identified as being connected to the tourniquet instrument, then the maximum allowable tourniquet pressure setting can be adapted and reduced to a much lower and safer maximum level without affecting the efficacy of the overall system. Also, the settings of certain alarm parameters within the instrument may be adapted upon automatic identification of the cuff connected to the instrument; for example, the maximum time limits allowed within the instrument for cuff inflation and for cuff deflation may be automatically adapted as a function of the size of the inflatable portion of the connected cuff, to provide a safety alarm signal in the event of a hazardous inability of the instrument to inflate or deflate the cuff within a normal maximum time period while also preventing the generation of false alarm signals.

Upon automatic identification of the specific size and type of cuff connected to the tourniquet instrument, and thus the size, shape and potential volume of the inflatable portion of the connected cuff, the settings of other parameters important in the regulation of tourniquet pressure can be adapted to improve the accuracy and responsiveness of pressure regulation. Further, if the cuff type can be automatically identified by a connected tourniquet instrument, then cuff-related data needed for a surgical record may be automatically generated and kept more easily and more accurately for inventory control and cuff utilization purposes. Such a record may also be used (in combination with recording of other parameters such as pressure used) to aid in establishing safer practice guidelines for the use of surgical tourniquets.

Cuffs and tourniquet instruments are made by various manufacturers, and it is presently possible for users to connect a tourniquet instrument made by one manufacturer to tourniquet cuffs made by other, unknown manufacturers. However, at least one tourniquet instrument known in the prior art has advanced safety and performance features that are specifically designed to work with tourniquet cuffs that are made by the same manufacturer (see, for example McEwen in U.S. Pat. No. 5,649,954 and McEwen in U.S. Pat. No. 5,681,339). Such safety features and operational features in a tourniquet instrument may not function, or may not function predictably or properly if a cuff from an unknown manufacturer is connected to the tourniquet instrument. Therefore, to avoid or minimize safety hazards, and to minimize potential legal liability for users and for the manufacturer of the tourniquet instrument, it is useful to have a tourniquet instrument that has the capability to automatically identify the manufacturer of the connected cuff and to accordingly adapt the settings of important safety parameters, operating parameters and messages and warnings to users. For example, if such an instrument detects that an unknown cuff type is connected, the instrument could display a warning to the user that certain important functions relating to safety and performance may be disabled. Also, a tourniquet system having the capability to automatically identify the type of connected cuff can permit the sale or lease of the instrument to a user on a peruse basis or in connection with the purchase of specified quantities of cuffs of a known and identifiable type. A variety of related functions could also be performed by a tourniquet instrument having the capability to automatically identify that connected cuffs were, or were not, made by a known manufacturer. For example if an unidentifiable cuff from an unknown manufacturer were connected to such an instrument, the instrument could be programmed to be non-operational; alternatively, the tourniquet instrument could be programmed to remain as operational as possible but warn of the use of an unidentifiable cuff and record the event, so as not to prevent or delay needed surgery.

Many tourniquet cuffs are designed for to be reused in multiple surgical procedures and are supplied by the manufacturer in a non-sterile state. Other tourniquet cuffs are designed for single use only, and are supplied in a sterile state (eg. 'Comforter™ Disposable Gel Cuff' sold by DePuy Orthopaedics Inc., 'Zimmer ATS Disposable Tourniquet Cuffs', Zimmer Patient Care, Dover, Ohio). These cuffs are used when sterility is required in the area where the cuff is applied, and when the cuff must not be re-used in order to prevent cross-contamination between patients. Such single-use sterile cuffs are designed to withstand a specified sterilization process (conducted by the manufacturer) and the typical stresses encountered in a single surgical procedure. Subsequent sterilization or processing may lead to hazardous conditions such as compromised sterility, deteriorated physical condition and possibly sudden failure of the cuff during surgery. In particular, exposure to high temperatures or ethylene oxide gas during sterilization can degrade the materials in these cuffs. Despite these risks, it is increasingly common for users to attempt to reprocess and re-use single-use sterile cuffs using cleaning processes that have not been approved or tested by the original manufacturer. For example, single-use sterile cuffs are routinely reprocessed by at least one company that uses a pasteurization process (which subjects the cuff to high temperature and humidity), and then returned to the user in a 'high-level disinfected' state, a non-sterile, lower state of cleanliness than when originally supplied by the manufacturer. Several other companies routinely reprocess single-use sterile tourniquet cuffs using ethylene oxide gas sterilization methods, returning the cuff in a surgically sterile state. Other sterilization methods (such as gamma or electron beam radiation and gas plasma processes) could conceivably be used to reprocess cuffs; however ethylene oxide gas is currently the most common and practical method due to availability of facilities and its suitability for small batch sizes. If exposure to such attempts to reprocess and re-sterilize sterile cuffs after surgical use could be automatically identified by the tourniquet instrument, the tourniquet instrument could adapt by activating various warning functions to alert the user and reduce potential hazards to the patient. No tourniquet cuff is known in the prior art that allows a tourniquet instrument to identify whether a connected cuff has been subjected to a subsequent re-sterilization process, and to adapt its operation accordingly.

Many prior-art tourniquet cuffs are color-coded to indicate size to a user by visual inspection. For example the 'Comforter™ Disposable Gel Cuff' sold by DePuy Orthopaedics Inc. has a color dot on the outer packaging label corresponding to the cuff size, but no indication of cuff size on the cuff itself. In several other types of tourniquet cuff (for example 'Zimmer ATS Disposable Tourniquet Cuffs', Zimmer Patient Care, Dover, Ohio), components permanently attached to the cuff (such as edge trim and/or tie ribbon) are made of a selected color of material corresponding to the cuff size. These identification means are solely visual and interpretable by the user who is familiar with the color coding scheme. No communication with a tourniquet instrument is automatically established by connection of the cuff to the instrument, and therefore the instrument necessarily cannot automatically adapt the settings of important parameters of operation and safety in response to the size and type of cuff connected to the instrument.

In U.S. Pat. No. 4,605,010, McEwen describes a tourniquet cuff that includes an electrical means for identifying remotely the physical characteristics of the cuff, as well as for remotely determining the circumference of the limb encircled by the cuff. To permit remote identification of cuff type, the McEwen '010 cuff includes electrically conductive components within the cuff structure, and requires an electrical connection as well as a pneumatic connection between the tourniquet cuff and the tourniquet instrument. Thus electrical power and an electrically conductive pathway are necessarily present within the cuff, in close proximity to the patient's limb encircled by the cuff. This can present a hazard to the patient under some circumstances. Also, inclusion of electrical components within the tourniquet cuff significantly increases the cost and complexity of manufacture of such cuffs, and their reliability at time of manufacture and subsequently during use. The prior art tourniquet cuff described by McEwen '010 includes means for allowing a connected tourniquet instrument to remotely determine the circumference of the limb encircled by the cuff. This permits the tourniquet pressure setting to be adjusted, based on the relationship between the physical characteristics of the remotely identified cuff and the remotely identified circumference of the limb encircled by the cuff. No other tourniquet systems in the prior art known to the inventors of the current invention establish a connection other than a pneumatic connection between the cuff and the instrument, such that information about the cuff can be received by the instrument and such that the settings of important safety and operating parameters of the instrument can be adapted in response. Further, fundamental problems inherent in the significantly increased cost and complexity, and in the inherently decreased reliability, of the apparatus described in McEwen '010, have prevented the commercial realization of any tourniquet systems incorporating apparatus such as described in McEwen '010.

No adaptive tourniquet cuff system is known in the prior art that includes provision for the tourniquet instrument to automatically identify physical characteristics of the connected tourniquet cuff and to adapt the settings of certain safety and operating parameters in response.

SUMMARY OF THE INVENTION

The present invention is directed to an adaptive tourniquet cuff system that comprises: a tourniquet cuff having a physical characteristic and including an inflatable bladder of a length greater than the circumference of a limb at a selected location; a cuff connector carried on the cuff and communicating pneumatically with the bladder for releasably connecting to a tourniquet instrument to establish a gas-tight passageway between the bladder and the tourniquet instrument; and an identifying collar including identification means indicative of the physical characteristic and detectable by the tourniquet instrument upon establishment of the gas-tight passageway. The tourniquet instrument may supply gas to the bladder through the gas-tight passageway at a pressure sufficient to stop arterial blood flow into the limb distal to the cuff at the selected location, and may adapt its operation in response to the detected physical characteristic of the cuff.

The methods and apparatus for carrying out the invention are described in detail below. Other advantages and features of the present invention will become clear upon review of the following portions of this specification and the drawings.

DETAILED DESCRIPTION OF THE PREFERRED EMBODIMENT

A specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 1:
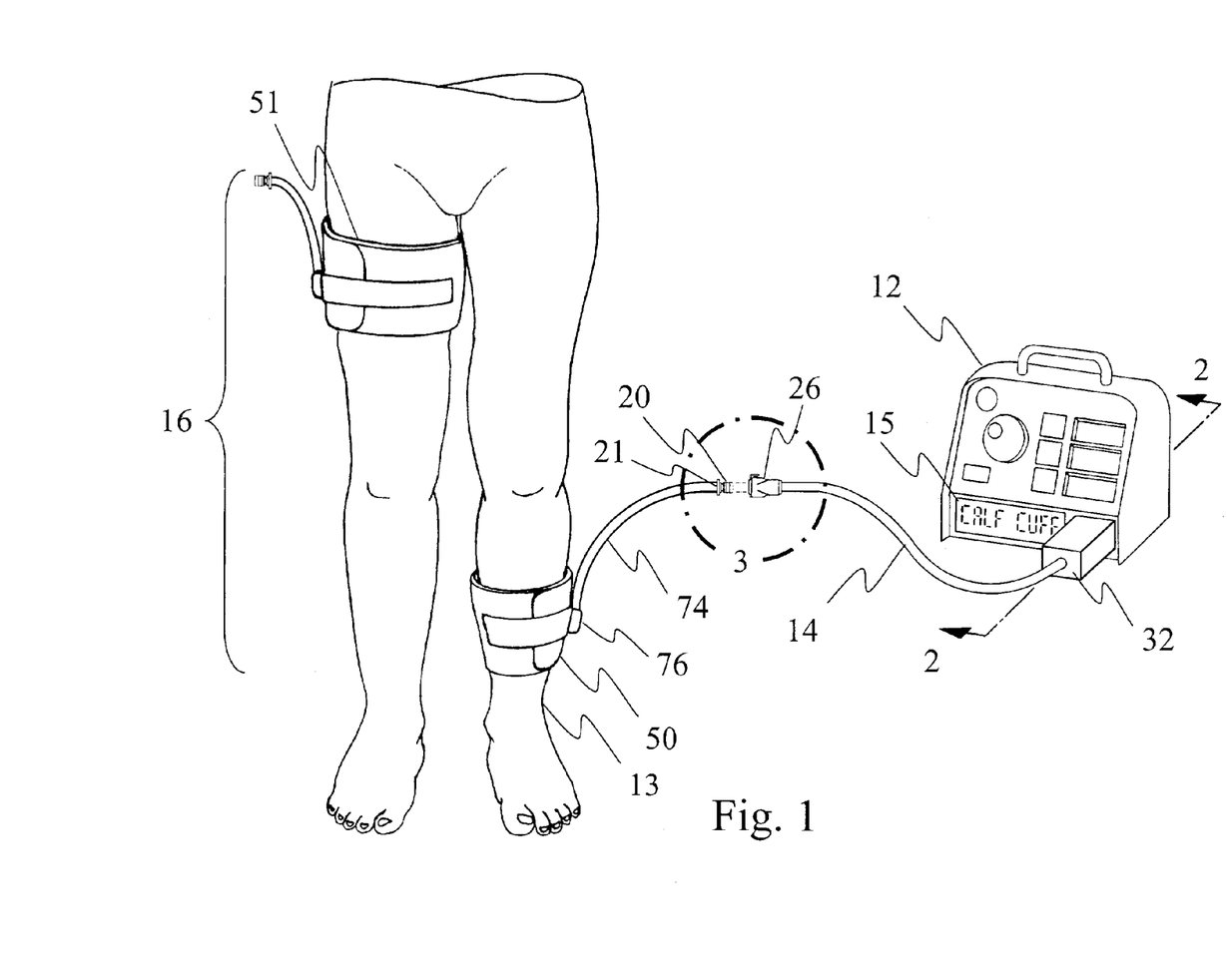
FIG. 1 is shows the tourniquet system with cuff identification means and a set of cuffs.

FIG. 1 shows the preferred embodiment of the invention consisting of tourniquet instrument 12, fill line assembly 14, and cuff set 16. Fill line assembly 14 includes fill line connector 26 and cuff identification module 32. Cuff set 16 comprises contour calf cuff 50 which has physical characteristics suitable for application to a lower leg within size and shape limits and contour thigh cuff 51 which has different physical characteristics suitable for application to a thigh within different size and shape limits. For clarity, physical characteristics of cuff 50 and cuff 51 include their size, shape, materials, and stiffness. Also for clarity, a physical characteristic may be predetermined to allow identification of the manufacturer of cuff 50 and 51 by tourniquet instrument 12 in the same way that a label allows visual identification of the manufacturer. Similarly, a physical characteristic may be predetermined to allow identification that cuffs 50 and 51 have been exposed to a predetermined process such as sterilization, in the same way that a process indicator label allows visual identification of exposure to the process. As described below cuff 50 includes an inflatable bladder portion and has a port manifold 76, hose 74, and cuff connector 20 permanently attached allowing a source of pressurized gas to be connected to the bladder. Cuff set 16 may comprise, for example, different size cuffs of similar design, a selection of cuffs designed for use on pediatric patients, or cuffs made by a particular manufacturer and are appropriate for use with the system. Each cuff in cuff set 16 has a cuff connector 20 and a distinctly colored identifying collar 21 indicating the cuff's distinct physical characteristic, both to the user (visually) and to instrument 12 as described below.

When the system is being used in surgery, at least one cuff from cuff set 16 is wrapped around the patient's limb 13 at a location proximal to the surgical site. Cuff 50 from cuff set 16 is shown in FIG. 1 connected to fill line assembly 14 by engaging cuff connector 20 (DSM2202, Colder Products Company, St. Paul, Minn.) with fill line connector 26 (a suitable connector being a modified version of a PMC 17-02 female locking connector made by Colder Products Company, St. Paul, Minn.). The embodiment shown is a "single port" system in which fill line assembly 14 provides a single gas-tight passageway from instrument 12 to cuff 50 for the purpose of inflating, sensing and regulating the pressure in, and deflating the cuff as required by the user (as is typical in many modern tourniquet systems). In the current invention fill line assembly 14 additionally provides a means for transmitting light between fill line connector 26 and cuff identification module 32, and a means for transmitting electrical signals between cuff identification module 32 and instrument 12. Fill line assembly 14 may be disconnected from instrument 12 for cleaning or replacement, therefore cuff identification module 32 incorporates means for making both pneumatic and electrical connections to instrument 12. Instrument 12 additionally includes a cuff identification display 15, both described below and shown in detail in FIGS. 2 and 3. The current invention is equally well suited to "dual port" systems (as described by McEwen in U.S. Pat. No. 4,469,099, also typical in modern tourniquet practice), which include two separate pneumatic connections to the cuff, one for sensing the pressure within the cuff and one for supplying pressurized gas to the cuff. With a dual port system, cuff identification module 32 and the associated light and electrical signal transmitting means may be incorporated into either pneumatic connection or both.

Figure 2:
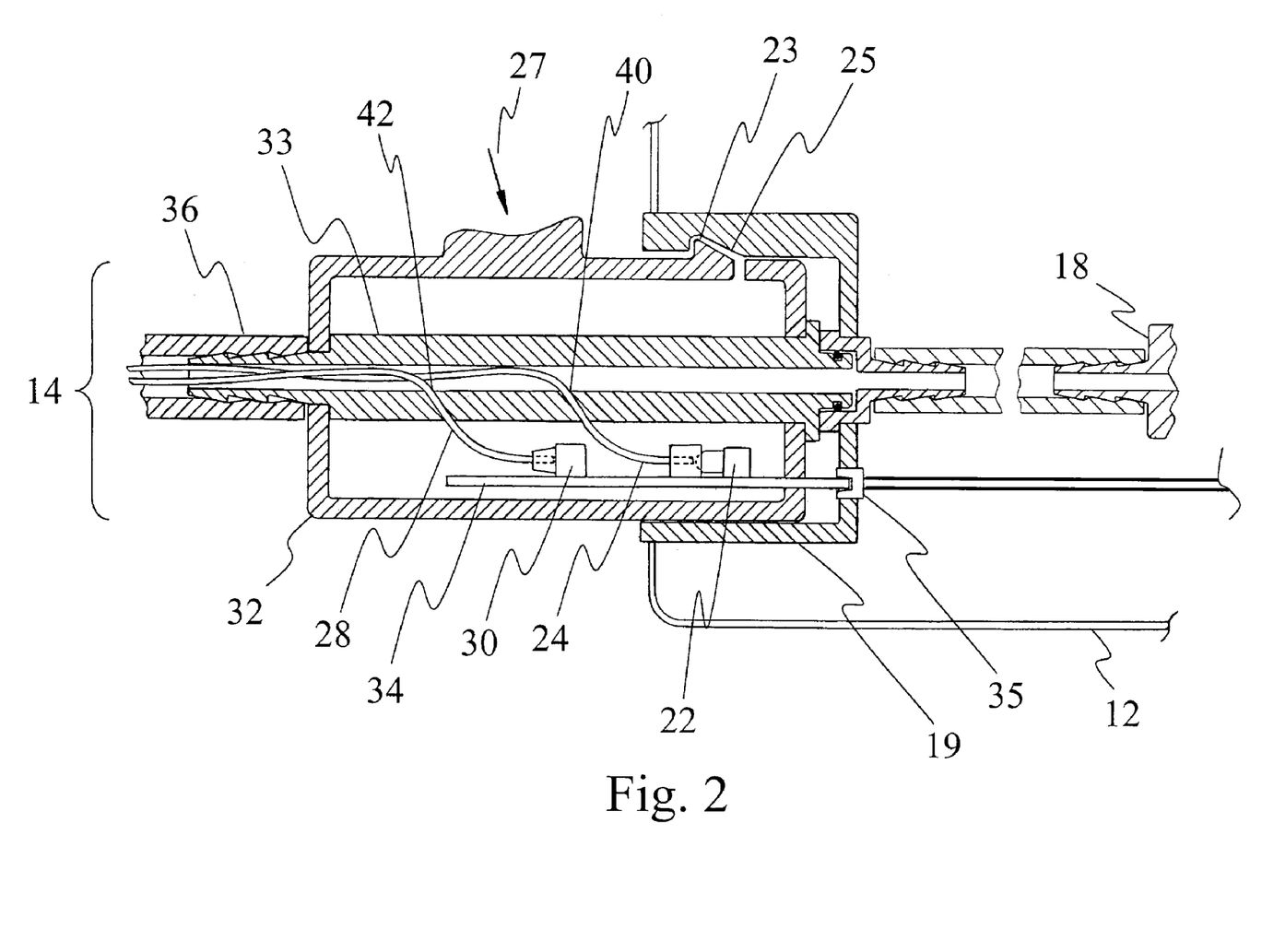
FIG. 2 is a section view through the connection arrangement between the fill line assembly and the tourniquet instrument, with block diagrams of the related electronic components in the instrument and the fill line assembly.

FIG. 2 shows a section view through the connection arrangement between cuff identification module 32 (included in fill line assembly 14) and tourniquet instrument 12. The body of cuff identification module 32 slides into socket assembly 19, which is rigidly mounted in instrument 12. To prevent accidental disconnection, locking tab 23 engages slot 25 in socket assembly 19 and upon engagement makes an audible click indicating to the user that the connection is complete. Locking tab 23 can be released by applying pressure in the direction of arrow 27 and pulling cuff identification module 32 out of socket assembly 19.

Figure 3:
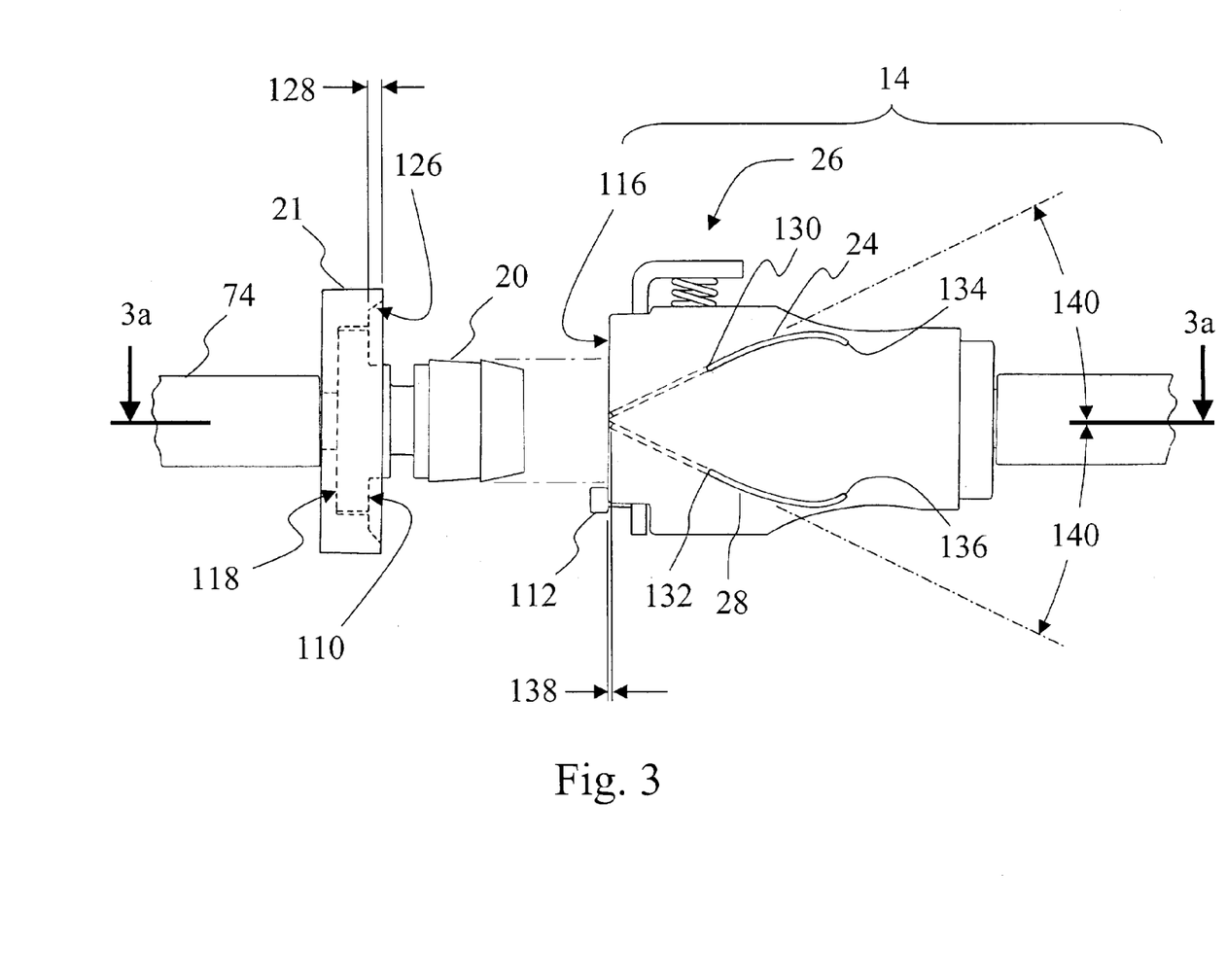
FIG. 3 is a detail view of the connection arrangement between the cuff and the fill line assembly with the connectors disengaged.

Fill line assembly 14 further comprises: hose 36 made of flexible polyurethane; fill line connector 26 shown in FIGS. 1 and 3; send fiber 24; and return fiber 28 (both made of 0.035" diameter plastic optical fiber PGR F3500, Moritex USA Inc., San Diego Calif.). Send fiber 24 and return fiber 28 lie within the lumen of hose 36 and are thus protected from damage. In the preferred embodiment hose 36 has an outside diameter of 0.25 inches and an inside diameter of 0.13 inches. Hose 36 is coupled to pneumatic connector 33, which in turn makes a releasable pneumatic connection to gas pressure source and regulating means 18 included in instrument 12 via socket assembly 19. Send fiber 24 and return fiber 28 pass through holes 40 and 42 and are bonded in place such that a gas-tight passageway is maintained from gas pressure source 18 to the lumen of hose 36 and in turn to the inflatable bladder of the cuff attached to the system. One end of send fiber 24 is optically coupled to three-color light emitting diode (LED) 22 (NSTM515AS, Nichia Corp., Tokushima, Japan) and one end of return fiber 28 is optically coupled to photodiode 30 (TSL 257, Texas Advanced Optoelectronic Solutions, Plano, Tex.). Light emitting diode 22 and photodiode 30 are controlled by additional hardware and software included in circuit board 34.

Cuff identification module 32 communicates with instrument 12 and cuff identification display 15 (see FIG. 1) via electrical connector 35 to indicate to a user the physical characteristic of the cuff connected to instrument 12. Those skilled in the art will appreciate that electrical connector 35 and cuff identification display 15 have communication pathways to the control electronics and system software of instrument 12 such that various functions of instrument 12 may be modified and information may be recorded based on the physical characteristic of the cuff connected to the system as detected by cuff identification module 32. It will also be appreciated that fill line assembly 14 and the associated software included in cuff identification module 32 can be easily adapted to function with a variety of different tourniquet instruments that can be equipped with socket assembly 19.

It will also be obvious that advancements and continued miniaturization and integration of color light emitting diodes and photodiodes may permit these elements to be readily incorporated in fill line connector 26 and that send and return optical fibers 24 and 28 could be replaced with electrical conductors. One current example of such miniature integrated color LED and photodiode reflective color sensors are the TTRS1722, TRS1755, and TRS1766 from Texas Advanced Optoelectronic Solutions, Plano, Tex.

Those skilled in the art will appreciate that incorporating electrical connector 35 into instrument 12 such that pneumatic and electrical connections to the fill line assembly are made simultaneously allows easy adaptation of instrument 12 to work with tourniquet cuffs using electrical identification means (such as those described by McEwen in U.S. Pat. No. 4,605,010) by use of a corresponding fill line assembly.

Figure 3A:
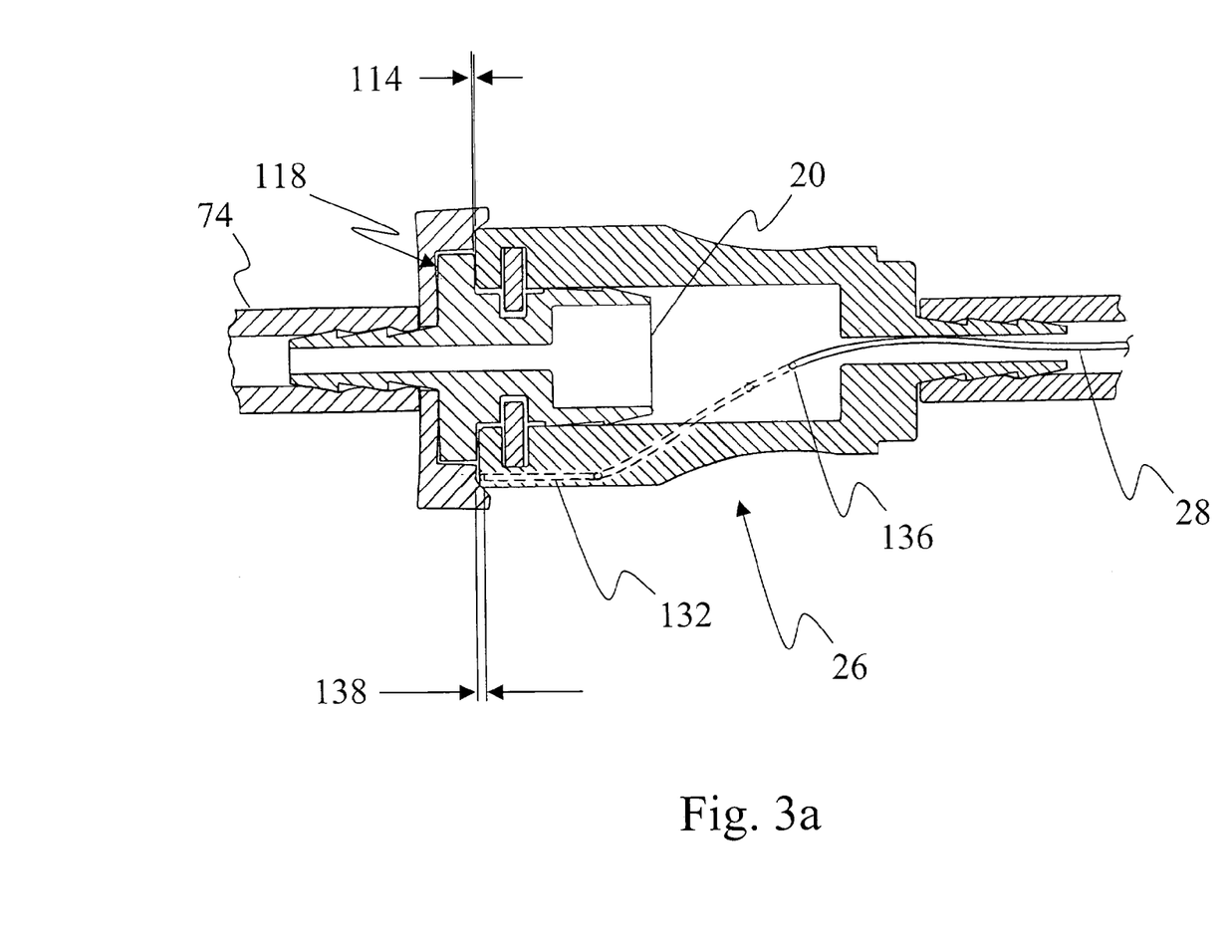
FIG. 3a is a section view from FIG. 3, showing the connectors engaged.

FIGS. 3 and 3a show the connection arrangement between cuff 50 and fill line assembly 14 (see FIG. 1). Cuff connector 20 is permanently attached to hose 74, which in turn is permanently attached to cuff 50 (see FIG. 1). Cuff connector 20 and fill connector 26 are a positive locking design and produce an audible 'click' when fully engaged, maintain a gas-tight passageway when rotated relative to one another about the lumen centerline and when subjected to tension along the lumen centerline, and require a releasing force substantially perpendicular to the lumen centerline in order to be disengaged. In particular, flange front surface 110 of cuff connector 20 actuates the locking pin 112 of fill line connector 26 and gap 114 (see FIG. 3a) between flange front surface 110 and fill connector front face 116 is typically 0.030 inches when the connectors are fully engaged. The design of connectors 20 and 26 is based on connectors described by McEwen in U.S. Pat. No. 5,649,954.

Figure 4:
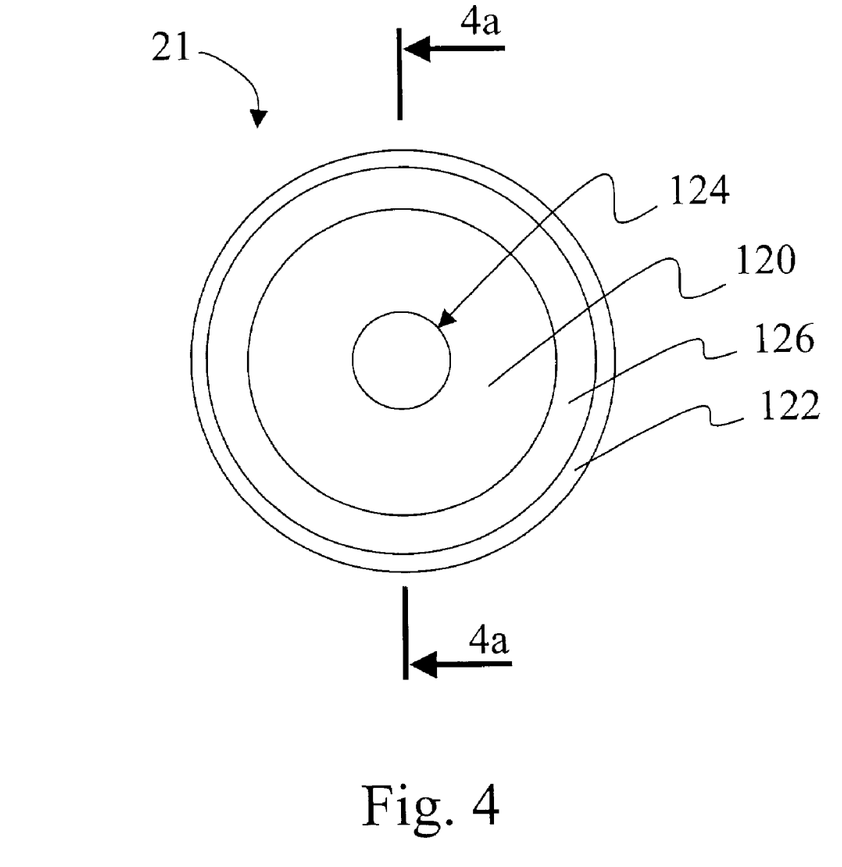
FIG. 4 is a detail view of the identifying collar.
Figure 4A:
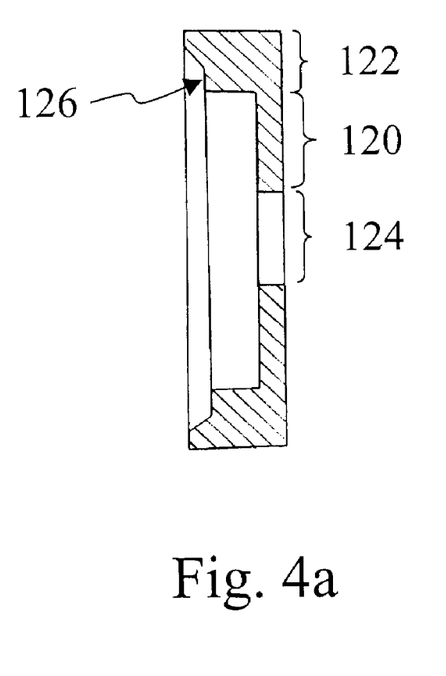
FIG. 4a is a section view of the identifying collar of FIG. 4.

Collar 21 (shown in detail in FIGS. 4 and 4a) is held against flange back surface 118 of cuff connector 20 when hose 74 is in place. Referring to FIGS. 4 and 4a, collar 21 comprises disc portion 120 and flange portion 122 with central hole 124 having a diameter greater than the inside diameter of hose 74 and less than the outside diameter of hose 74. Collar 21 is made entirely of electrically insulating, non-conductive material of selected color and opacity, with the color corresponding to a chosen physical characteristic of the cuff.

Referring to FIGS. 3 and 3a, identifying surface 126 of collar 21 extends proud of flange front surface 110 of cuff connector 20 by overlap 128 so that identifying surface 126 is in contact with fill line connector front face 116 when the connectors are fully engaged. Overlap 128 is greater than gap 114 and disc portion 120 of collar 21 is of selected stiffness such that when the connectors are engaged, disc portion 120 of collar 21 flexes, acting as a spring maintaining contact between identifying surface 126 and fill connector front face 116 when the connectors are engaged and also when tensile and bending forces typically encountered during use are applied between the connectors.

For adaptation to the current invention, fill connector 26 has holes 130 and 132 and holes 134 and 136 extending from the outer surface to the inner bore of fill connector 26. Holes 130, 132, 134, and 136 have diameters matching send fiber 24 and return fiber 28, and the fibers are bonded into the holes such that their ends lie within distance 138 (approximately 0.030 inches) from the fill connector front face 116. This physical configuration of send fiber 24 and return fiber 28 within fill connector 26 permits light emitted by send fiber 24 to illuminate identifying surface 126 and light reflected from identifying surface 126 to be transmitted to instrument 12 by return fiber 28. Holes 130 and 132 are each arranged at angle 140 (26 degrees) determined by the optical properties of send and return fibers 24 and 28 to optimize the collection of reflected light by return fiber 28. Thus when connectors 20 and 26 are fully engaged, a pneumatic pathway is established between cuff 50 and instrument 12 and at the same time light can be transmitted between collar 21 and instrument 12 allowing cuff 50 to be identified as described below. Both the pneumatic pathway and the light transmission pathway are maintained if the connectors are rotated relative to one another about the lumen centerline or subjected to tension along the lumen centerline.

Maintenance of contact by the selected stiffness of disc portion 120 and the selected interference between identifying surface 126 and fill connector front face 116 as described above helps minimize interference and signal saturation due to high intensity ambient light (for example if the coupled connectors 20 and 26 fall under the beam of surgical lamps during use). The body of fill line connector 26 is preferably opaque to minimize interference and signal saturation due to high intensity ambient light. Collar 21 is manufactured to have consistent color and opacity such that the light reflected from the collar remains within predetermined limits when cuff connector 20 and collar 21 are rotated relative to fill line connector 26 about the lumen centerline, and such that the light reflected from mass produced colored collars is also within predetermined tolerance limits.

It will be appreciated by those skilled in the art that the color and properties of collar 21 are selected depending on the physical characteristic to be identified. For example if only the cuff manufacturer needs to be identified, then all cuffs in cuff set 16 would have the same color of collar 21. If different sizes and types of cuffs within cuff set 16 need to be identified, then each distinct size and type would have a particular color of collar 21. If exposure to a selected process such as ethylene oxide (EO) sterilization must be identified, collar 21 may be coated on identifying surface 126 with an active indicating compound which responds to the selected process by changing color. For example, identifying surface 126 may be coated with EO sterilization indicating ink (Tempil Inc., South Plainfield N.J.) which is red and remains stable throughout packaging, gamma radiation or electron beam sterilization by the manufacturer, and use. Upon exposure to a subsequent EO sterilization process, identifying surface 126 changes to a brown color. It will be appreciated by those skilled in the art that identifying surface 126 may alternately be formed by applying a separate material containing indicating ink such as an adhesive film (eg. Steri-Dot #361001, Propper Manufacturing Company, Long Island City, N.Y.) or, as chemical indicators of EO exposure continue to be developed, formed by including the indicating compound in the material used to form collar 21.

It will also be appreciated that collar 21 may be integrated into cuff connector 20 for ease of manufacture, in which case the integrated collar and connector may be made of a non-electrically conducting material of selected color and opacity for each physical characteristic requiring identification. It will also be appreciated that other connector arrangements are possible which establish a pneumatic communication between the cuff and the instrument and a means for transmitting light between the cuff and the instrument. For example send and return fibers 24 and 28 may be arranged such that light is transmitted through collar 21 (if collar 21 is made from translucent material) rather reflected from collar 21 as described above. Also the current invention may be adapted for dual port tourniquet systems (as described in the background) that comprise a single connector with two separate gas passageways and send and return fibers 24 and 28 applied to a selected passageway as shown in FIGS. 3 and 3a, or a pair of send and return fibers applied to each passageway as shown in FIGS. 3 and 3a.

It will also be appreciated that because collar 21 provides means for identifying the cuff without interfering with or modifying the pneumatic connection means, the invention may be adapted to various other types of pneumatic connectors other than the particular type shown in the preferred embodiment.

Referring to FIGS. 1, 2, and 3, cuff identification module 32 operates as described below to determine the type of cuff connected to instrument 12 as indicated by the color of identifying collar 21. Cuff identification module 32 communicates with cuff identification display 15 and to other components within instrument 12 to indicate the type of cuff connected to instrument 12. When instrument 12 is switched on cuff identification module 32 is activated. In operation cuff identification module 32 activates LED 22 to emit a continuous series of red, green, and blue light pulses in succession (for example a 0.5 millisecond pulse of each color with a 1.5 millisecond delay between colors). The light output from LED 22 is optically coupled to send fiber 24 and transmitted to connector 26. The light pulses generated by LED 22 are emitted from send fiber 24 within connector 26 and illuminate identifying collar 21 when cuff connector 20 is engaged in fill line connector 26 to establish the gas-tight passageway between cuff 50 and instrument 12.

One end of return fiber 28 is optically coupled to photodiode 30, the other end is terminated within connector 26 such that light reflected from identifying collar 21 can be transmitted to photodiode 30. In the absence of identifying collar 21 ambient light is transmitted to photodiode 30.

Cuff identification module 32 monitors the intensity level of light detected by photodiode 30. By recording the detected intensity levels at the times when red, green and blue light is being emitted from LED 22 and when LED 22 is inactive, cuff identification module 32 can compute the relative intensities of red, green and blue light reflected from identifying collar 21 and the intensity of ambient light detected when LED 22 is inactive. The detected intensity levels of ambient light recorded when LED 22 is inactive are used by cuff identification module 32 to compensate for variations in ambient lighting conditions and detect error conditions such as the complete saturation of photodiode 30. The computed relative intensity levels of red, green and blue light reflected by identifying collar 21 are compared by cuff identification module 32 to predetermined ranges of relative intensities stored within cuff identification module 32 and corresponding to each cuff in cuff set 16. The cuff type is determined when a predetermined number of reflected light pulses (for example five consecutive series of red, green and blue light pulses) all have relative intensities falling within the predetermined range matching the cuff type. Once identified, the cuff type and/or related predetermined information may be displayed on cuff identification display 15 and recorded within cuff identification module 32, information from other components within instrument 12 such as time and date, pressure setting, and tourniquet inflated time may also be recorded by cuff identification module 32.

The colors corresponding to the various different cuff types in cuff set 16 are selected to produce distinct relative intensity levels of reflected red, green and blue light. Cuff identification module 32 may be initially calibrated in order to adjust the stored predetermined ranges of relative intensities corresponding to specific cuff types to compensate for changes in component specifications and manufacturing variations. Calibration may be performed by using a series of reference colored connectors, and similarly re-calibration may be performed in the field by the user or by service personnel.

An example of the operation of cuff identification module 32 is as follows. When a specific type of cuff from cuff set 16 having a red identifying collar 21 is connected to fill line assembly 14, green and blue light pulses generated by LED 22 are absorbed by the red identifying collar 21 to a greater degree than the red light pulses generated by LED 22. Consequently the intensity of the red light pulses reflected from the red identifying collar 21 relative to the intensity of the reflected green and blue light pulses is greater. Cuff identification module 32 will identify the attached cuff as corresponding to a specific type having a red identifying collar 21 by comparing the relative intensities of the light reflected from the red colored cuff connector and sensed by photodiode 30 to a predetermined selection of stored relative intensity values. Once the color of identifying collar 21 has been identified or it has been determined that no identifying collar 21 with a identifiable color is present, predetermined signals are sent by cuff identification module 32 to instrument 12 via electrical connector 35, and instrument 12 automatically adapts selected functions and parameter settings accordingly.

Cuff identification module 32 in conjunction with instrument 12 also operates to detect potentially hazardous conditions. During operation cuff identification module 32 continuously monitors the absolute intensity levels of the reflected red, green and blue light pulses and the intensity level of ambient light when LED 22 is inactive. A sudden drop in intensity levels indicates possible disengagement of connectors 20 and 26 or a kink in hose 36. If hose 36 and fibers 24 and/or 28 are kinked such that the specified minimum bend radius of the fiber(s) is exceeded, the intensity level of light detected by photodiode will be reduced as light can no longer be transmitted by the optical fibers. If a sudden reduction in detected light levels is concurrent with falling cuff pressure and a corresponding high demand for pneumatic pressure from instrument 12, warning of a possible disconnection at connectors 20 and 26 may be activated. If signal loss is not accompanied by loss of pressure or high demand for pneumatic pressure from instrument 12, warning of a possible kink in hose 36 may be activated.

Cuff identification module 32 can, by recording the intensity levels of detected light over a number of uses, enable various automatic system optimization and self-calibration functions. For example a gradual reduction in detected light levels over time or a number of uses may indicate wear and degradation of the fill line assembly 14 and a service advisory message may be displayed. Similarly, changes in light levels corresponding to a particular type of cuff over time may activate a self-calibration function or service advisory.

Once the cuff has been identified or it has been determined that an unidentifiable cuff is connected, the operation of instrument 12 is adapted accordingly. Some examples of the automatic adaptation of the operation of instrument 12 are as follows:

As an example of the physical characteristic of the cuffs being type and size, cuff identification module 32 and instrument 12 may be programmed to identify and adapt to a predetermined set of colors of identifying collar 21 each corresponding to a cuff size and type in cuff set 16. In this example, contour thigh cuff 51 (FIG. 1) is equipped with a blue identifying collar 21 and upon identification of the blue color by cuff identification module 32, instrument 12 adapts the default pressure setting to 250 mmHg, which has been found to be appropriate for most patients when this particular cuff is used. To inform the user, cuff identification display 15 is adapted to show 'Contour Thigh Cuff' and 'Default Pressure 250 mmHg' messages. Similarly, contour calf cuff 50 is equipped with a yellow identifying collar 21, and when this cuff is connected and identified, instrument 12 automatically adapts the default pressure setting to 200 mmHg, a more appropriate pressure setting for contour calf cuff 50, and display 15 is adapted to show 'Calf Cuff' and 'Default Pressure 200 mmHg' messages. In addition, the settings of selected parameters affecting the operation of instrument 12 (such as alarm delay times and pressure regulation limits as described by McEwen in U.S. Pat. No. 4,469,099) may be automatically adapted to better suit the smaller inflated volume of contour calf cuff 50 as compared to contour thigh cuff 51. If a cuff that is not equipped with an identifying collar 21 having one of the predetermined colors (and therefore does not belong to cuff set 16), instrument 12 adapts the default pressure setting to zero and displays an 'Unknown Cuff Type' message in display 15; the user must then set the tourniquet pressure manually.

As an example of the physical characteristic of the cuff being the cuff manufacturer, all cuffs made by the cuff manufacturer may be equipped with red identifying collars 21 and form cuff set 16. Upon connection of any cuff in cuff set 16, instrument 12 adapts display 15 to show an 'Approved Cuff' message and adapts predetermined parameter settings (such as tubing obstruction signals as described by McEwen in U.S. Pat. No. 5,861,339) to suit the physical characteristics of manufacturer's cuffs. If the connected cuff is not equipped with a red identifying collar 21, instrument 12 adapts display 15 to show 'Unapproved Cuff Type' and 'Line Occlusion Alarms Disabled' messages. Additionally, instrument 12 may be programmed to be non-operational, to operate only after user intervention, or operate for a limited number of surgical cases only with unidentifiable cuffs connected. Instrument 12 may also be programmed to record the number of times unapproved cuffs are used.

As an example of the physical characteristic of the cuff being whether the cuff has been subjected to a subsequent re-sterilization process, cuffs in cuff set 16 may be equipped with identifying collars 21 having a process indicating ink coating on identifying surface 126 (see FIGS. 4 and 4a). Upon identification of the color of identifying surface 126 representing exposure to the re-sterilization process, instrument 12 adapts display 15 to show warning messages 'Used Cuff' and 'Cuff may not be sterile'. Additionally, instrument 12 may be programmed to be non-operational, to operate only after user intervention, or operate for a limited number of surgical cases only with reprocessed cuffs connected. Instrument 12 may also be programmed to record the number of times reprocessed cuffs are used.

It will be appreciated that a combination of different physical characteristics may be identified by using a plurality of identifying surfaces, each having a send/return fiber pair. For example if both cuff type and exposure to ethylene oxide sterilization must be detected, type could be identified by a distinct color of connector 20 (as described in the parent application) and exposure to EO sterilization could be identified by identifying collar 21 as described above. If multiple identifying surfaces are used, detected colors may be compared to enable various automatic system optimization and self-calibration functions. For example if identifying collar 21 has a common color for all cuffs in cuff set 16 indicating that the cuff has not been exposed to EO sterilization and cuff connector 20 has a predetermined color corresponding to the cuff type, the relative intensity level of light reflected from identifying collar 21 may also be used as a reference to adjust the stored predetermined ranges of relative intensities corresponding to specific cuff types.

It is to be understood that the invention is not to be limited to the details herein given but may be modified within the scope of the appended claims.

The invention claimed is:

1. An adaptive tourniquet cuff system, comprising:
a tourniquet cuff having a plurality of predetermined physical characteristics including a cuff shape, a cuff width dimension, a cuff length dimension that is greater than the circumference of a limb at a selected location, and an inflatable bladder having a size dimension; and
a cuff connector carried on the cuff and communicating pneumatically with the bladder for releasably connecting to a second connector to establish a gas-tight passageway between the bladder and a tourniquet instrument,
wherein the cuff connector includes a flexible collar mounted to the cuff connector and colored to be indicative of one predetermined physical characteristic of the plurality of predetermined physical characteristics of the cuff and detectable by the tourniquet instrument upon establishment of the gas-tight passageway, wherein the collar flexes and engages the second connector when the cuff connector is connected to the second connector.

2. The adaptive tourniquet cuff system of claim 1 and including the tourniquet instrument, wherein the tourniquet instrument includes means for supplying gas to the bladder through the gas-tight passageway in accordance with a plurality of parameters of safety and operation, and at a maximum pressure not greater than a maximum pressure level.

3. The adaptive tourniquet cuff system of claim 2 wherein the tourniquet instrument further produces a signal indicative of the detected predetermined physical characteristic of the cuff.

4. The adaptive tourniquet cuff system of claim 2 wherein the tourniquet instrument further adapts one of the plurality of parameters of safety and operation in response to the detected physical characteristic of the cuff.

5. The adaptive tourniquet cuff system of claim 2 wherein the tourniquet instrument further adapts the maximum pressure level in response to the detected physical characteristic.

6. The adaptive tourniquet cuff system of claim 1 wherein the connector and collar are integrated and entirely formed of electrically insulating material.

7. The adaptive tourniquet cuff system of claim 1 wherein the connection of the cuff connector and second connector defines a gap between those connectors and through which gap light is transmitted, the collar further including a flange portion adapted to block ambient light from illuminating the gap.

8. The adaptive tourniquet cuff system of claim 1 wherein the one predetermined physical characteristic is the length dimension of the cuff.

9. The adaptive tourniquet cuff system of claim 1 wherein the one predetermined physical characteristic is the size dimension of the inflatable bladder.

10. An adaptive tourniquet cuff system, comprising:
   a sterile tourniquet cuff having a shape, a width, a length, an inflatable bladder and a plurality of predetermined physical characteristics;
   a cuff connector carried on the cuff and communicating pneumatically with the bladder for releasably connecting to a tourniquet instrument to establish a gas-tight passageway between the bladder and the tourniquet instrument,
   wherein the cuff connector includes identification means indicating a color value that is detectable by the tourniquet instrument upon establishment of the gas-tight passageway, the color value of the cuff connector identification means being changeable as a result of sterilization of the cuff.

11. The adaptive tourniquet cuff system of claim 10, wherein the predetermined physical characteristic is one of the plurality of predetermined parameters formed by the process of manufacturing the cuff.

12. An adaptive tourniquet cuff system, comprising:
   a tourniquet cuff having an inflatable bladder and having a predetermined physical characteristic;
   a connector carried on the cuff and communicating pneumatically with the bladder for releasably connecting the cuff to a tourniquet instrument connector to establish a gas-tight interface between the bladder and the instrument wherein the interface defines a gap between the connector and the tourniquet instrument connector,
   an identifying collar colored to indicate the predetermined physical characteristic, the color being detectable by the tourniquet instrument upon establishment of the gas-tight interface;
   a tourniquet instrument for supplying pressurized gas to the bladder through the connector, wherein the instrument includes detection means responsive to the color of the collar for producing a signal indicative of the physical characteristic, and wherein
   the collar includes a flange portion for blocking ambient light from illuminating the gap.

* * * * *